United States Patent [19]
Izraelevitz et al.

[11] Patent Number: 5,618,729
[45] Date of Patent: Apr. 8, 1997

[54] AUTOMATED SYSTEM AND METHOD FOR ESTIMATING ANTIBIOTIC EFFECTIVENESS FROM DRUG DIFFUSION TESTS

[75] Inventors: David Izraelevitz, Chelmsford; Karen S. Cochand, Manchester, both of Mass.

[73] Assignee: The Analytic Sciences Corporation, Reading, Mass.

[21] Appl. No.: 471,377

[22] Filed: Jun. 6, 1995

Related U.S. Application Data

[62] Division of Ser. No. 323,906, Oct. 17, 1994.

[51] Int. Cl.$^6$ ............................... C12M 1/34; C12M 1/18
[52] U.S. Cl. .................... 435/288.7; 435/287.7; 435/808; 382/128
[58] Field of Search ................... 435/29, 32, 33, 435/34, 288.3, 288.4, 288.7, 287.7, 808; 382/110, 128, 133; 356/384

[56] References Cited

U.S. PATENT DOCUMENTS 3,757,299  9/1973  Perry ........................................ 382/128

FOREIGN PATENT DOCUMENTS 207739  1/1987  European Pat. Off. .................. 435/32

OTHER PUBLICATIONS

Boshard et al. "Alternative Quality Control Parameters for Autobac Susceptibilty Testing Disk: ... " Journal of Clinical Microbiology, vol. 13 (May 1981). pp.814–817.

Clontz. "Image analysis application to agar diffusion assays." American Clinical Laboratory, (Aug. 1992), pp.10–11.

Giacca et al. "Multivariate Analysis of Antibiograms for Typing Pseudomonas aeruginosa." Eur. J. Clin. Microbiol., vol.6 (Oct. 1987), pp.552–558.

Hejblum et al. "Automated Interpretation of Disk Antibiotic Susceptibility Tests with the Radial Profile Analysis Algorithm." J. Clin. Microbiol., vol. 31, (Sep. 1993), pp. 2396–2401.

HSIA. "A semiautomated quantitative antibiotic disk testing system." American Clinical Laboratory, (May 1994), pp. 28–29.

Murray et al. "Comparison of a Highly Automated 5-h Susceptibility Testing System, the Cobas-Bact, ... " J. Clin. Microbiol., vol. 25 (Dec. 1987), pp. 2372–2377.

*Primary Examiner*—Wllliam H. Beisner
*Attorney, Agent, or Firm*—Wolf, Greenfield & Sacks, P.C.

[57] ABSTRACT

A method and apparatus for estimating drug effectiveness from a drug diffusion sample are provided. The drug diffusion sample includes a plate having a medium containing a test organism and a plurality of antibiotic disks positioned on the plate in a medium. An inhibition zone surrounds each of the antibiotic disks after a prescribed incubation period. The drug diffusion sample is illuminated, and an image of the drug diffusion sample is acquired with a video camera. The image is analyzed by determining the locations of the antibiotic disks, determining the average brightness and the brightness variance of the image in a region surrounding each of the antibiotic disks, and estimating the radius of the inhibition zone surrounding each of the antibiotic disks from the average brightness and the brightness variance. The radius of the inhibition zone is indicative of drug effectiveness.

9 Claims, 8 Drawing Sheets

AUTOMATED SYSTEM AND METHOD FOR ESTIMATING ANTIBIOTIC EFFECTIVENESS FROM DRUG DIFFUSION TESTS

This application is a division of application Ser. No. 08/323,906, filed Oct. 17, 1994, entitled AUTOMATED SYSTEM AND METHOD FOR ESTIMATING ANTIBIOTIC EFFECTIVENESS FROM DRUG DIFFUSION TESTS, and now Pending.

FIELD OF THE INVENTION

This invention relates to techniques for evaluating the effectiveness of antibiotics in inhibiting the growth of a test organism and, more particularly, to methods and apparatus for automatically estimating antibiotic effectiveness using image analysis techniques.

BACKGROUND OF THE INVENTION

In developing a treatment strategy for an infectious disease, a physician must know which antibiotics are most effective in either killing the organism or at least inhibiting or retarding its further growth. The conventional approaches to evaluating the effectiveness of an antibiotic against an organism are typically categorized as: 1) tube dilution assays, and 2) drug diffusion tests.

In the tube dilution assay approach, each antibiotic under consideration is diluted by a series of two-fold dilutions, and the diluted antibiotics are deposited in a set of test tubes. Each tube is then inoculated with the test organism in question and is examined after a 24 hour incubation period to see if the organism has been killed. In this way, the minimal inhibitory concentration is determined. Since data is available about the attainable blood levels for any antibiotic, the minimal inhibitory concentration provides a direct mechanism for determining the potential value and necessary dosage for effective treatment.

The most common drug diffusion test for antibiotic susceptibility is the Kirby-Bauer method. This test involves the use of a Petri plate containing an agar medium whose surface has been swabbed with the test organism. About a dozen disks impregnated with each antibiotic under test are distributed on the surface of the Petri plate. After an incubation period, the diameter of the zone of inhibited growth is measured with calipers. Well-known tables relate the diameter of the inhibition zone to the likely resistance of the organism to the antibiotic.

In many circumstances, the Kirby-Bauer method is preferable to the tube dilution assay approach. Difficulties with tube dilution assays include the fact that certain organisms or media are not amenable to analysis using this method. However, manual measurement of inhibition zones using the Kirby-Bauer method is time consuming and is subject to error.

Systems utilizing image analysis techniques for automating drug diffusion tests have been proposed. G. Hejblum et al in *J. Clin. Microbiol.*, Vol. 31, No. 9, September 1993, pages 2396–2401 describe a system in which the radial profile of each inhibition zone is determined. The shape of the radial profile is analyzed to determine the inhibition zone diameter. Systems using image analysis techniques for automating drug diffusion tests are also described by L. Clontz in "Image Analysis Application to Agar Diffusion Assays", *American Clinical Laboratory*, August 1992, pages 10 and 11, and by W. Hsia in *American Clinical Laboratory*, May 1994, pages 28 and 29. The prior art systems are understood to include one or more disadvantages, including the failure of the system to accurately determine inhibition zone diameter for a wide variety of conditions and different organisms.

SUMMARY OF THE INVENTION

According to the present invention, a method for estimating drug effectiveness from a drug diffusion sample is provided. The drug diffusion sample comprises a plate having a medium containing a test organism and a plurality of antibiotic disks positioned on the plate in the medium. An inhibition zone surrounds each of the antibiotic disks after a prescribed incubation period. The method of the invention comprises the steps of illuminating the drug diffusion sample, acquiring an image of the drug diffusion sample, and analyzing the image with an electronic digital computer. The step of analyzing the image comprises the steps of determining the locations of the antibiotic disks in the image, determining the average brightness and the brightness variance of the image in a region surrounding each of the antibiotic disks and estimating the radius of the inhibition zone surrounding each of the antibiotic disks from the average brightness and the brightness variance. The radius of the inhibition zone is indicative of drug effectiveness. The radius of the inhibition zone may range from the radius of the antibiotic disk, indicative of no effectiveness, to an arbitrary maximum radius, indicative of a high degree of effectiveness.

The locations of the antibiotic disks are preferably determined as follows. The number of pixels in the image covered by the antibiotic disks is determined. Next, the pixels in the image are ordered from lowest brightness to highest brightness. Then, a threshold value is determined such that all the pixels in the image covered by the antibiotic disks have brightness values less than the threshold value. Then, a binary image is defined wherein each pixel has a value of one if the brightness of the pixel is less than the threshold value and a value of zero if the brightness of the pixel is greater than the threshold value. The areas and the coordinates of the centroids of connected regions having a value of one in the binary image are determined. The $N_d$ largest connected regions having a value of one in the binary image are identified as the antibiotic disks, where $N_d$ is the number of antibiotic disks on the plate. Preferably, the radius of each of the antibiotic disks is also determined.

According to another feature of the invention, the drug diffusion sample is illuminated with radiation in a selected wavelength range. In a preferred embodiment, the drug diffusion sample is illuminated with radiation in the red portion of the visible wavelength range.

The radius of the inhibition zone is preferably estimated as follows. For each radius value, r, between the radius of the antibiotic disk and a maximum radius, an inside ring between r–d and r, and an outside ring between r and r+d, where d is a small value, are defined. For selected radius values, a first ratio of brightness variance to the minimum brightness variance between the radius of the antibiotic disk and the maximum radius is determined. Those radius values for which the first ratio is greater than a first threshold value are retained. Next, a second ratio of average brightness in the outside ring to average brightness in the inside ring is determined for selected radius values. Those radius values for which the second ratio is greater than the second threshold value are retained. Then, for selected radius values, a first error value representative of the average squared difference between the brightness at each pixel in the inside ring and the maximum brightness is determined. In addition, a second error value representative of the average squared difference between the brightness of each pixel in the outside ring and the average brightness in the outside ring is determined. Finally, the radius of the inhibition zone is selected as a retained radius value for which the sum of the first error value and the second error value is minimized.

The image of the drug diffusion sample is preferably displayed on a display screen of a video display system with the estimated radius of each inhibition zone. According to a further feature of the invention, the estimated radius of the inhibition zone of a selected antiotic disk may be changed in response to a user positioning a cursor at a desired location on the display screen and operating a pointing device, such as a mouse.

BRIEF DESCRIPTION OF DRAWINGS

For a better understanding of the present invention, reference is made to the accompanying drawings, which are incorporated herein by reference and in which.

DETAILED DESCRIPTION

Figure 1:
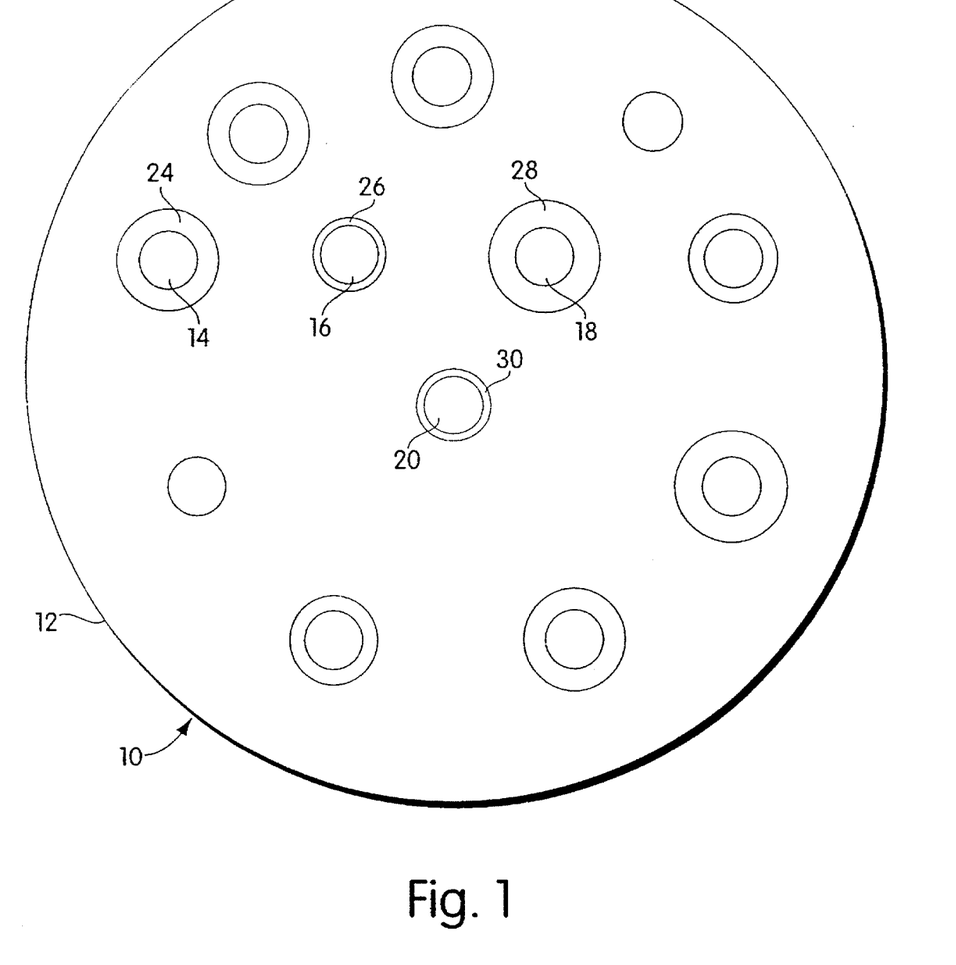
FIG. 1 is a schematic representative of a drug diffusion sample for automated analysis in accordance with the present invention.

An example of a drug diffusion sample 10 for analysis in accordance with the method and apparatus of the present invention is shown in FIG. 1. A light-transmissive plate 12, such as a Petri plate, is coated with a medium, such as agar, and a test organism is applied to the medium. Antibiotic disks 14, 16, 18, 20, etc. impregnated with the different antibiotics being tested are distributed over the plate in a predetermined pattern. In one example, plate 12 contains a pattern of twelve antibiotic disks. However, other numbers and patterns of antibiotic disks can be utilized.

After an incubation period, such as 24 hours, inhibition zones 24, 26, 28, 30 etc. surround the respective antibiotic disks. The inhibition zone is a zone in which the antibiotic on the antibiotic disk has inhibited growth of the organism. The inhibition zone appears as a relatively transparent area surrounding the antibiotic disk, whereas areas of the plate 12 outside the inhibition zones are relatively opaque. The diameter of each inhibition zone is an indication of the effectiveness of the respective antibiotic in inhibiting growth of the test organism. The radius of the inhibition zone may range from the radius of the antibiotic disk (indicative of no effectiveness) to an arbitrary maximum, typically 25 to 30 mm, (indicative of a high degree of effectiveness). The inhibition zones are generally circular, but may have an irregular shape due to various factors, such as for example, an uneven distribution of the medium on the plate 12.

Figure 2:
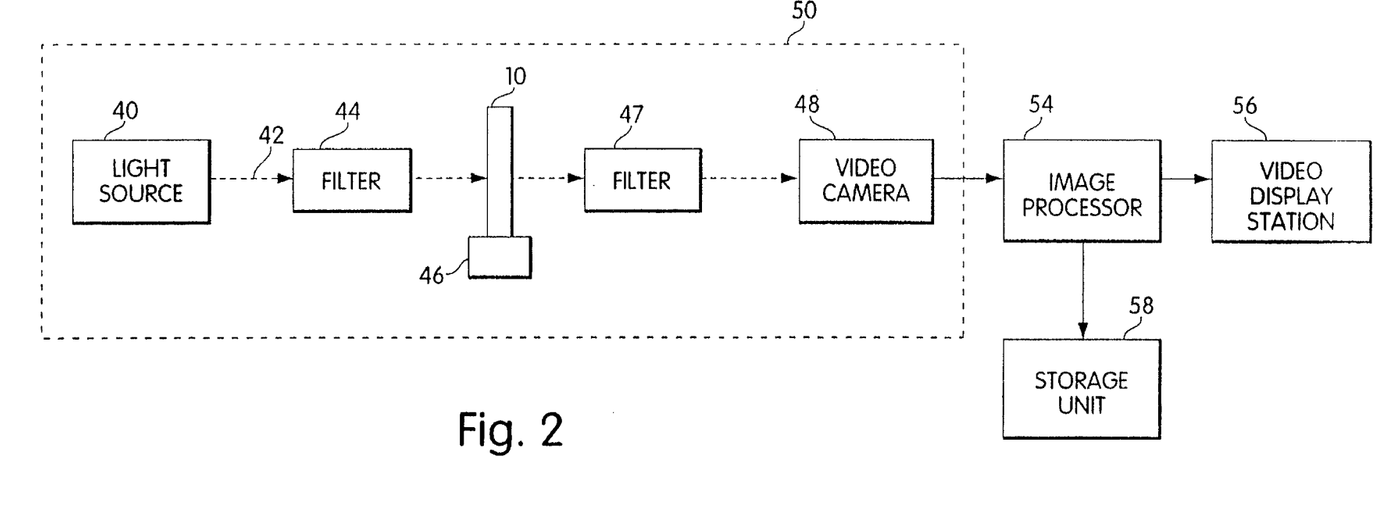
FIG. 2 is a block diagram of an automated system for estimating antibiotic effectiveness in accordance with the present invention

A block diagram of an automated system for estimating antibiotic effectiveness from drug diffusion tests is shown in FIG. 2. A light source 40 directs a light beam 42 through an optional optical filter 44 for illumination of a drug diffusion sample 10 as shown in FIG. 1 and described above. The drug diffusion sample 10 is mounted in a holding fixture 46 that permits light to pass through light-transmissive portions of the drug diffusion sample. Light transmitted through the drug diffusion sample passes through an optional second optical filter 47 and is intercepted by a video camera 48 which acquires one or more images of the drug diffusion sample 10.

The light source 40 can be any suitable source which illuminates the drug diffusion sample 10 relatively uniformly and which provides acceptable contrast between the inhibition zones and surrounding areas. The filter 44 is optional and can be used to select a wavelength range that provides good contrast between the inhibition zones and the surrounding areas of the drug diffusion sample. The second filter 47 performs a similar function and has the advantage that it blocks ambient light outside its passband from reaching video camera 48. In general, the automated system may use filter 44, filter 47, both filters 44 and 47, or no filter. When no filter is used, the light source 40 may be selected to provide the desired spectrum, and ambient light should be blocked from reaching the video camera 48. Wavelengths in the red portion of the visible spectrum have been found to provide relatively high contrast. In a preferred embodiment, light source 40 comprises multiple (up to 10) 15 watt fluorescent bulbs covered by a light diffusing glass cover, and filter 44 or filter 47 selects wavelengths in the range of 650 to 800 nanometers. A suitable filter is manufactured by Lee, Filter No. 182. While transmission of light from source 40 through the drug diffusion sample 10 to the video camera 48 is preferred, any illumination configuration which permits the video camera 48 to acquire an acceptable image can be utilized.

The video camera 48, for example, can be a black and white CCD camera, such as a Panasonic WV-BL200 and a Computar 6 mm video lens. In one embodiment, a light shield 50 surrounds light source 40, filter 44, drug diffusion sample 10 and video camera 48 to block stray light from reaching the video camera 48.

The output of video camera 48 is applied to an image processor 54 which may include a frame grabber such as an OCULUS OC-MX one megabyte frame grabber manufactured by CORECO, and an electronic digital computer, such as a type an IBM compatible 486/33 personal computer. The frame grabber digitizes and stores an image of the drug diffusion sample 10. The computer analyzes the digitized image to provide an estimate of the radius of each of the inhibition zones. The image and the estimated radius of each inhibition zone may be displayed on a video display station 56 and may be stored in a storage unit 58 for future reference.

The result of conversion of the camera output to electronic form is a matrix of intensity values, typically between the 0 and 255, indexed by coordinates x and y, called an image, $I(x,y)$. Each element of $I(x,y)$ is called a pixel. The term pixel is also used as a unit of distance between two locations on the image. Typically, the index x ranges from 0 to 639, and the index y ranges from 0 to 511. In the following discussion, the image is assumed to be oriented such that x increases from left to right, and y increases from top to bottom.

Figure 6:
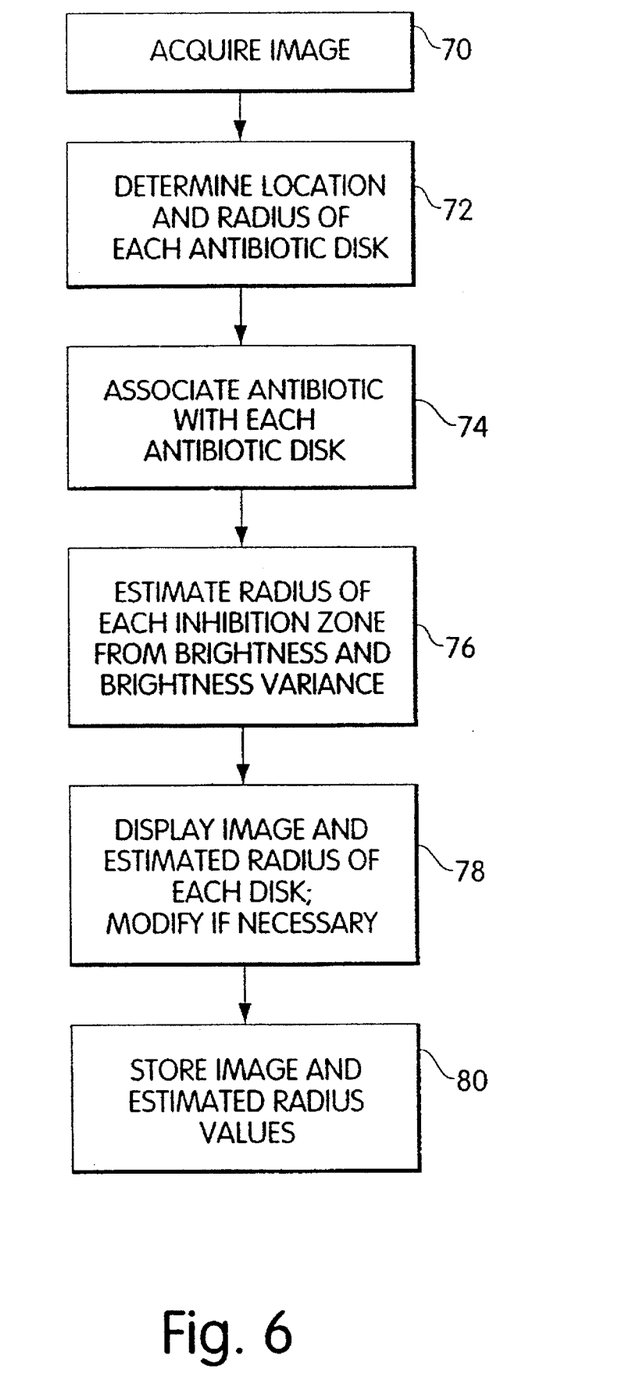
FIG. 6 shows a flow diagram of the process for estimating antibiotic effectiveness in accordance with the invention.

The operations executed by the system of FIG. 2 are shown in the flow diagram of FIG. 6. An image of the drug diffusion sample is obtained in step 70. A disk location module generates estimates of the locations of the centers of the antibiotic disks as represented in the image (step 72). In addition, this module generates estimates of the radius of each disk on the image, which are refinements from initial estimates solely based on disk dimensions. Thus, if each antibiotic disk is indexed by i, the output of the disk location module is a set of triplets $(x_i, Y_i, r_i)$, which are respectively the x coordinate and y coordinate of the center of each disk and the radius of the disk in pixels. A disk labeling module generates a mapping from each triplet $(x_i, Y_i, r_i)$ to one of a predefined set of antibiotics in step 74. The mapping is performed by use of a prerecorded template which indicates the nominal location of each specific antibiotic disk on the plate 12. Thus, the disk labeling module augments the input triplet by adding a fourth field, which is the antibiotic descriptor, $L_i$.

An inhibition zone estimation module generates an estimate of the radial distance from the center of each antibiotic disk in which an antibiotic is diffused sufficiently that it no longer kills the test organism (step 76). This module associates with each antibiotic disk a characteristic inhibition zone radius, $R_i$.

An analysis review module permits an operator to evaluate the results of the inhibition zone estimation module (step 78). The operator may modify the estimated inhibition zone radius as described below.

A storage and retrieval module permits an operator to store and later retrieve both the acquired image and the results of the disk location, labeling and inhibition zone estimation modules for later validation or review (step 80).

The system shown in FIG. 2 and described above is used in two different modes, calibration and measurement. The calibration mode is used to estimate the conversion factor between distances computed from the electronic image (i.e., from pixel coordinates) to metric measurements, such as millimeters. The calibration mode can also be used to identify inhomogeneities in the illumination of the drug diffusion sample 10. In the calibration mode, an empty Petri plate is placed in the holding fixture 46. The light which passes through the plate is recorded by the video camera 48. The analog output of the video camera is digitized and stored in the image processor 54. For an empty Petri plate, the image is a uniformally bright circle. Since the diameter in millimeters of the Petri plate is known, analysis of the diameter of the electronic image of the plate in pixels provides a proportionality constant, $\alpha$, that relates image distances in pixels to actual plate distances in millimeters. In addition, a measurement can be made of any inhomogeneity in illumination or acquisition across the field of view. The measured inhomogeneities are used to normalize images during the measurement mode.

In the measurement mode, a drug diffusion sample 10 is placed in the holding fixture 46. The light which passes through the drug diffusion sample 10 is recorded by the video camera 48. The analog output of the video camera is digitized and stored by the image processor 54. The data representing the acquired electronic image is passed to the image processing software and is analyzed as described below.

Figure 7:
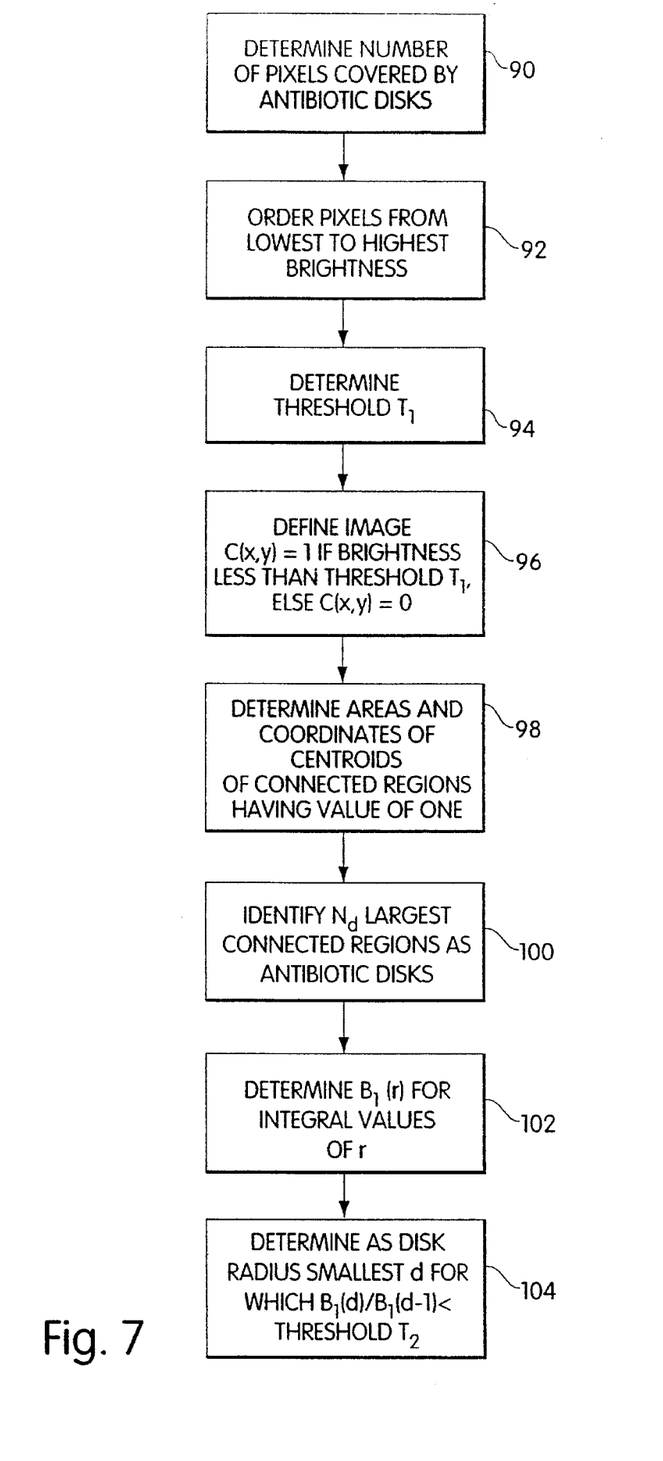
FIG. 7 show a flow diagram of the software for determining the location and radius of each of the antibiotic disks.

From the acquired image, the location of each antibiotic disk is calculated by the disk location module as follows, with reference to FIG. 7. A database populated off line contains the nominal radii (in millimeters) of the antibiotic disks, $r_d$, used and the radius of the Petri plate, $R_p$. This database also contains the number of antibiotic disks on the plate, $N_d$. From this information, the ratio of the area covered by the disks to the total area of the Petri plate is calculated as $(N_d r_d^2)/R_p^2)$. Since the relationship between distances in pixels and metric distances is known from the calibration step, the number of pixels nominally covered by the antibiotic disks is determined in step 90. This number is given by $\pi R^2 (N_d r_d^2)/R_p^2)$, where R is the radius of the Petri plate in pixels as computed during the calibration step.

The pixels inside the Petri plate are ordered from lowest brightness value to highest brightness value in step 92. A threshold value, $T_1$, is then computed such that $\pi R^2 (N_d r_d^2)/(R_p^2)$ pixels have brightness values less than or equal to $T_1$ (step 94). In step 96, a new image, $C(x,y)$, is constructed which satisfies:

$$C(x,y)=1 \text{ if } I(x,y)<T_1 \text{ else } C(x,y)=0 \qquad (1)$$

From this binary image, an auxiliary image $L(x,y)$ is generated such that each connected region in image $C(x,y)$ having of a value of 1 is assigned a unique label (see, for example, *Computer Vision*, Ballard and Brown, p. 151). For each connected region, i, the total area in number of pixels, $A_i$, as well as the coordinates of its centroid, $X_i$ and $Y_i$ is computed in step 98 (see, for example, *Digital Picture Processing*, Rosenfeld and Kak, p. 288). The $N_d$ connected regions with the largest areas are identified as the locations of the antibiotic disks in the image (step 100). This approach has the advantage of being insensitive to relative changes in illumination and does not depend on fixed brightness thresholds.

The second task of the disk location module is the refinement of the location of the boundary of each antibiotic disk in the image. An initial estimate of the boundary is provided by a circle of radius $\alpha r_d$ by converting the known radius of the disk from millimeters to pixels. Since the antibiotic disk is opaque, the disk should be dark in the image, while the image should become substantially brighter outside the disk. This transition from very dark to bright is very narrow, typically on the order of one or two pixels, and is composed of those pixels which only partially cover the disk. Thus, at this transition, there is a dramatic increase in brightness over a one to two pixel interval.

The refinement of the location of the boundary of the disk in the image is preferably computed as follows, with reference to FIG. 7. First, an array $B_1(r)$ is computed in step 102 which contains, for location (r), the average brightness of all pixels which are at a distance r from the disk center, where r is truncated to the nearest integral value of pixels. Beginning with a distance value of $d=\alpha r_d/2$, i.e., half the nominal radius of the disk, the smallest index d is found such that the ratio of $B_1(d)$ to $B_1(d-1)$, i.e., the distance value immediately lower, is above a threshold, $T_2$, typically 1.1. A large ratio indicates the inception of a dramatic increase in brightness. This location is used as a refined estimate of the disk radius (step 104).

Figure 8:
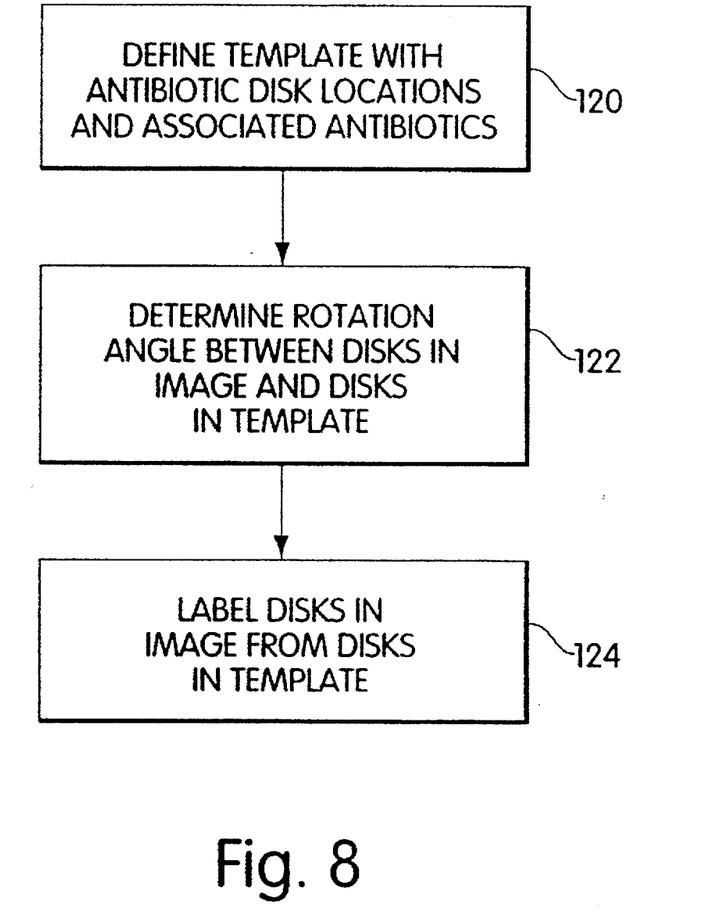
FIG. 8 shows a flow diagram of the software for associating an antibiotic with each of the antibiotic disks.

After the location of the antibiotic disks and refinement of the disk radius values, the next step is the association of each disk with an antibiotic by the disk labeling module, as shown in FIG. 8. Because the antibiotic disks are deposited in a regular geometric orientation by a mechanical device, the relative locations of the disks on the plate are roughly known. Thus, a template can be generated prior to processing which contains the x and y coordinates in millimeters of each antibiotic disk in the plate with respect to the center of the plate (step 120). As a preliminary step, the x and y coordinates are converted to pixel distances using the conversion ratio $\alpha$.

In order to label the antibiotic disks on the image, a rotation angle between the disks as placed on the plate and the locations of the disks in the template must be estimated (step 122). The system addresses this labeling process in one of two ways. A first approach is to orient the plate on the fixture so that the same antibiotic disk is always in roughly the same location. As an example, assume that the plate is placed on the fixture such that the disk containing penicillin is located on the image so that it has the smallest x coordinate. The location of this disk is easily found by calculating the x coordinate of each disk as located by the previously described algorithm. A rotation angle with respect to the plate center is then computed that matches the measured location of the penicillin disk with the location of the same antibiotic disk in the template information. This rotation is then applied to each disk in the image. Finally, the distance between each rotated disk location and the disk location in the template is computed. The matching is performed by finding a correspondence that minimizes an error metric between the template disk locations and the rotated image disk locations. One possible error metric is to minimize the maximum distance between any two matched disk locations.

A second approach does not require placement of the plate in any preferred orientation. Each possible matching between the disk locations in the image and the disk locations in the template is examined. For each match, the necessary rotation angle is computed as described above. The same error metric is used as an evaluation of the quality of the superposition. The match retained is the one for which the error metric is minimized. This approach requires that there be no rotational symmetries in the relative positions of the antibiotic disks that can lead to multiple candidate orientations. If such symmetry is present, it can be broken by deletion of a disk from the assay, by addition of an extraneous disk, or by addition of fiducial marks that can be detected by the system.

When the rotation angle has been determined, the disks in the image are labeled in step 124 with the antibiotic descriptor, $L_i$, from the antibiotic disk information in the template.

After a specific antibiotic has been associated with each antibiotic disk on the plate, the inhibition zone estimation module makes an estimate of the maximum distance from the center of the disk at which the density of organism growth has been inhibited. This estimation is performed for each antibiotic disk individually.

Figure 3:
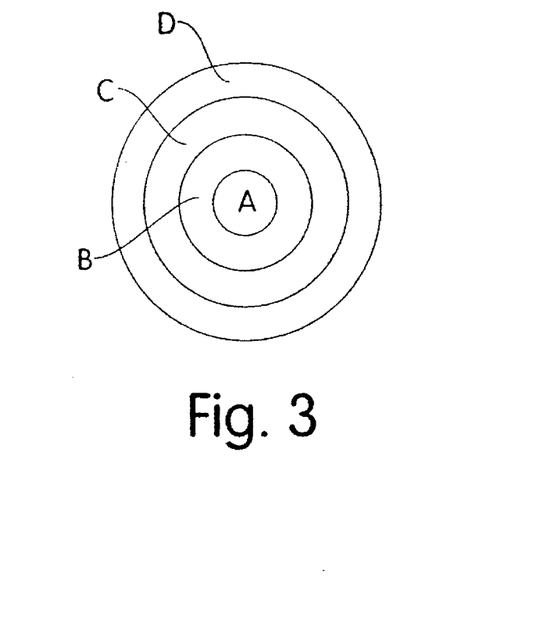
FIG. 3 is a schematic diagram that illustrates the regions surrounding a single antibiotic disk

In order to better describe the estimation procedure, the typical characteristics of the regions surrounding near an antibiotic disk are described. Four sets of pixels typically form concentric rings centered on the disk center, as shown in FIG. 3. The estimation procedures makes use of the average brightness and variance characteristics of each region, which are summarized in Table 1 below.

TABLE 1

| Relative brightness and variance characteristics | | |
|---|---|---|
| Region | Brightness | Variance |
| A | very low | very low |
| B | very high | low |
| C | medium | high |
| D | low | medium |

In region A, the pixels are within the antibiotic disk. Since the disks are opaque, the measured brightnesses of pixels in this region are relatively dark, and there is small variation about a constant value. Thus, the variability in measured brightness is small as well. In region B, the antibiotic has completely destroyed the organism population, and the plate is transparent and uniform. Therefore, the measured brightness is high and the variability about this brightness value is small. At the transition between region A and region B, the variance increases because some pixels partially cover the disk. In region C, growth of the test organism is partially inhibited. Although the plate is not transparent, it is much clearer than areas unaffected by the antibiotic. The measured brightness is lower than in region B because of the occlusion by the organism culture. Variability in brightness in this region is typically higher than in region B because of spotty growth by the organism and also because pixels will cover areas of mixed no-growth and partial growth. Finally in region D, the antibiotic was completely ineffective. Here the medium is partially opaque, leading to a lower measured brightness than in regions B or C, while the variability about the average is somewhere between that of regions B and C. Variations in measured brightness in region D are typically due to differential growth of the organism from non-uniform deposition of the culture prior to incubation. The typical average brightness $B_1(r)$ as a function of radius is shown as curve 60 in FIG. 4A. The brightness variance $B_2(r)$ as a function of radius is shown as curve 62 in FIG. 4B.

Because a clinician must be assured that a prescribed antibiotic will be effective against the organism, the inhibition zone is typically defined as the boundary between regions B and C, where the antibiotic was completely effective, rather than the boundary between regions C and D, where the antibiotic began to affect the reproductive rate of the organism. Sometimes, region C is very small because the antibiotic is either completely effective or completely ineffective. However, at other times the region C can cover several millimeters. The present invention is specially designed to handle both cases. The approach used in the present invention to reliably estimate the radius, $r_{BC}$, at the transition between regions B and C is described below. The estimation of the radius, $r_{AB}$, at the transition between regions A and B has been already described above.

Figure 5:
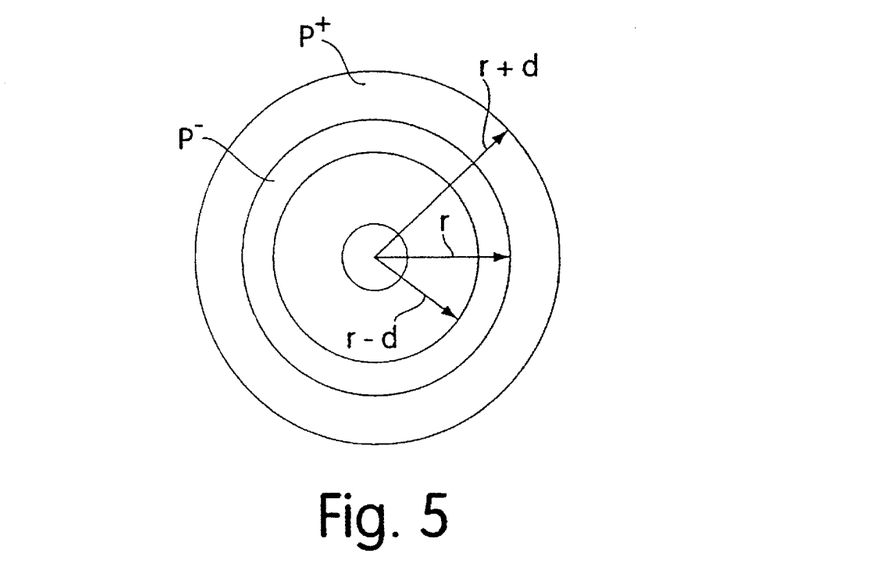
FIG. 5 is a schematic diagram that illustrates the inner and outer rings utilized during image analysis.

Several properties of the transition between regions B and C are used to estimate its location. With reference to FIG. 5, an inside ring $P^-$ is defined as the set of pixels which are at a distance between $r_{BC}-d$ and $r_{BC}$ from the disk center, for a small value of d. An outside ring $P^+$ is defined as the set of pixels at a distance between $r_{BC}$ and $r_{BC}+d$. The following properties assist in determining the proper value of $r_{BC}$:

1. The local variance at the B-C transition, $B_2(r_{BC})$, should be large in relation to the variance within region B.
2. The average brightness within inside ring $P^-$ should be high relative to the average brightness within outside ring $P^+$.
3. The average brightness within inside ring $P^-$ should be close to the highest brightness recorded in the region around the antibiotic disk under study.

4. The brightness variance within the inside ring $P^-$ should be small. The brightness variance within inside ring $P^-$ would be large if this ring contains a transition between regions.

5. The brightness variance within outside ring $P^+$ should be small. The brightness variance within outside ring $P^+$ would similarly be large if this ring contains a transition between regions.

Figure 9:
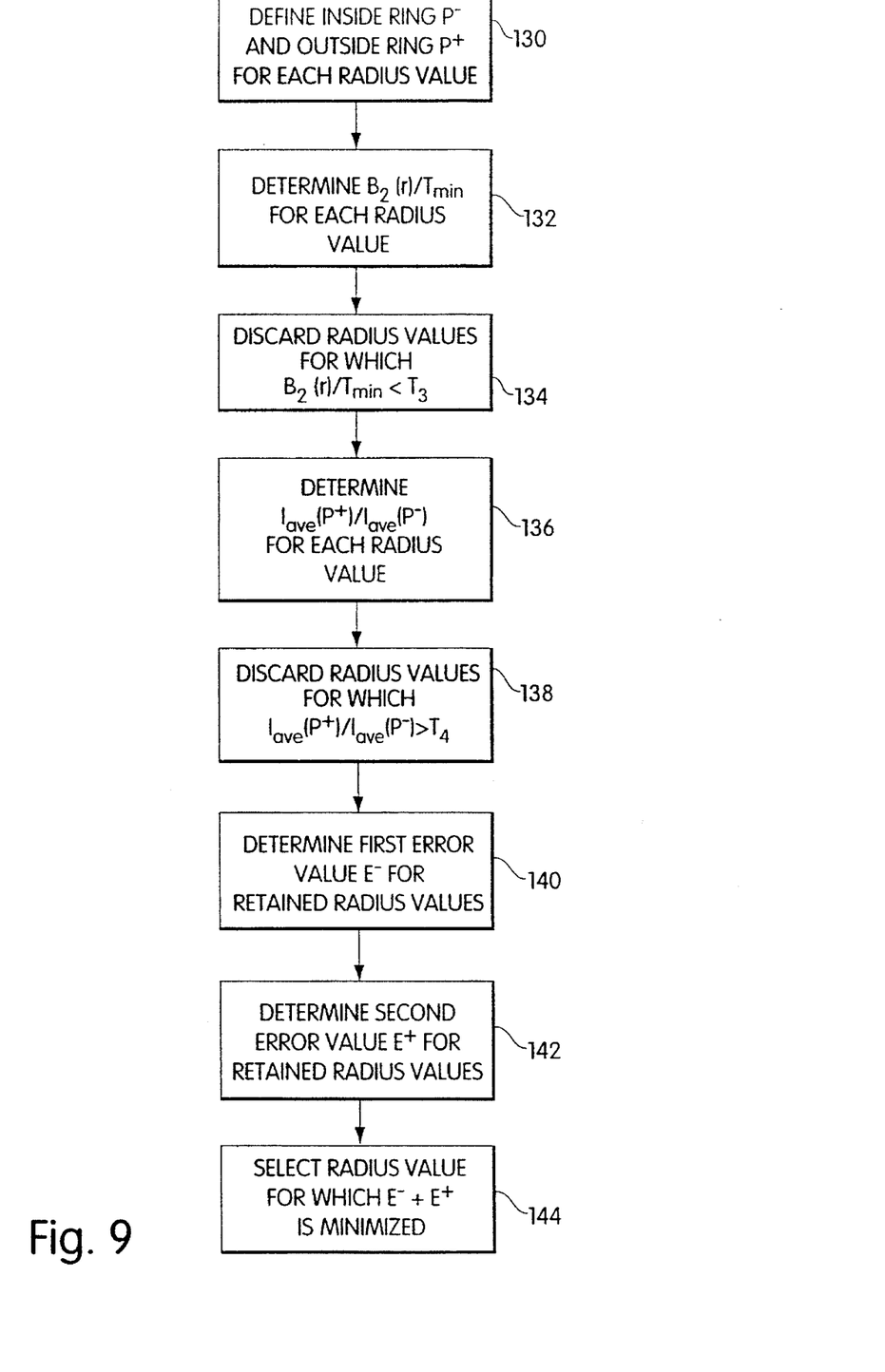
FIG. 9 show a flow diagram of the software for estimating the radius of each inhibition zone.

The approach described below and illustrated in FIG. 9 is designed to determine that radius value which best satisfies the properties listed above. For each radius value r in pixels between radius $r_{AB}$ and a user specified maximum radius $r_{max}$, typically set to be the pixel distance equivalent of 25–30 millimeters, the inside ring $P^-$ and the outside ring $P^+$ are constructed in step 130 using a value of d which is equal to the radius of the antibiotic disk, i.e., $r_{AB}$. The only exception to the above construction of rings $P^-$ and $P^+$ is that if the radius value r is less than $d+r_{AB}$, the boundary of ring $P^-$ is adjusted such that it does not include any pixels in the antibiotic disk. If this measure is not taken, small inhibition zones are inaccurately processed, frequently leading to over-estimates of the inhibition zone radius.

Figure 4A:
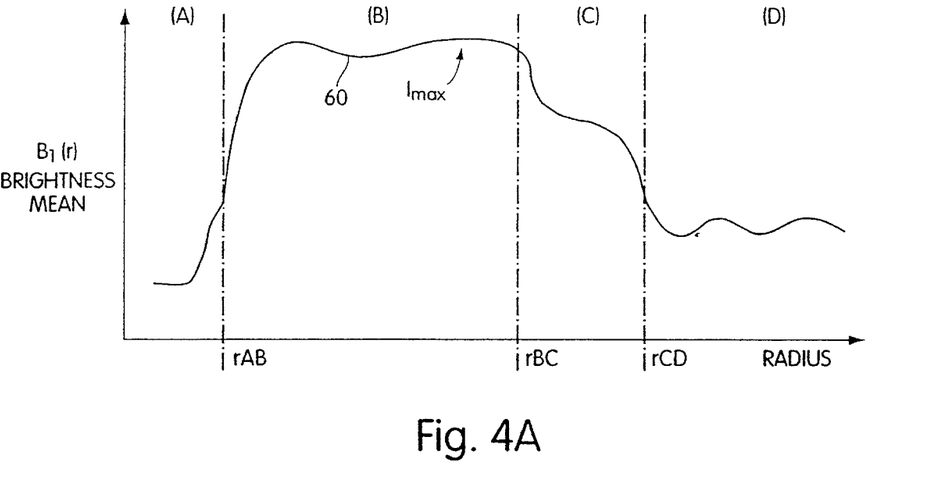
FIGS. 4A and 4B are graphs of brightness and brightness variance, respectively, in the regions surrounding the antibiotic disk of FIG. 3.
Figure 4B:
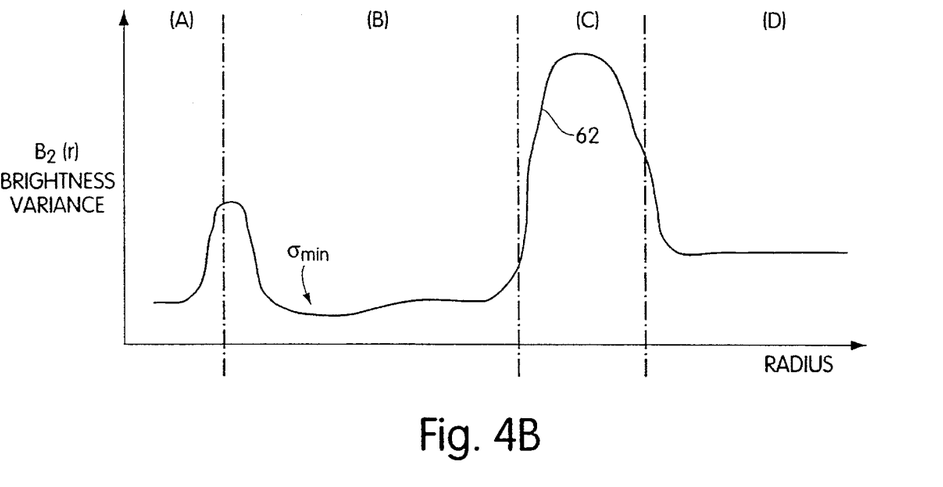

From FIGS. 4A and 4B, the location of the highest average brightness, $I_{max}$, and the location of the lowest variance $\sigma_{min}$ outside of region A will be inside region B. $I_{max}$ and $\sigma_{min}$ are computed as follows.

$$I_{max} = \max_{r_{AB} < r < r_{max}} B_1(r) \quad (2A)$$

$$\sigma_{min} = \min_{r_{AB} < r < r_{max}} B_2(r) \quad (2B)$$

At each candidate integral value r between radius $r_{AB}$ and maximum radius $r_{max}$, the ratio $B_2(r)/\sigma_{min}$ is computed in step 132. All those radius values of r for which the ratio is less than a predetermined threshold $T_3$, typically 1.5, are disqualified from being estimates of the radius $r_{BC}$ at the B-C transition (step 134).

The next step is to calculate the average brightness for all pixels within the inside ring $P^-$, and within the outside ring $P^+$. Since the average brightness for all pixels within inside ring $P^-$, $I_{ave}(P^-)$, is expected to be higher than the average brightness within outside ring $P^+$, $I_{ave}(P^+)$, the ratio $I_{ave}(P^+)/I_{ave}(P^-)$ is computed for each remaining radius value in step 136. Radius values which satisfy $I_{ave}(P^+)/I_{ave}(P^-) > T_4$, where $T_4$ is a threshold value, are disqualified in step 138 from being estimates of the radius $r_{BC}$. The threshold $T_4$ is controlled by the operator, but is usually set to 0.95.

To decide among the remaining radius values, an error metric is designed to incorporate properties 3 to 5 above. Since the pixels within inside ring $P^-$ should be close to maximum brightness $I_{max}$, the average squared difference between the brightness at each pixel within inside ring $P^-$ and the maximum brightness $I_{max}$ is computed in step 140 as follows.

$$E^- = \frac{\sum_{(x,y) \in P^-} (I(x,y) - I_{max})^2}{N(P^-)} \quad (3)$$

where $N(P^-)$ is the number of pixels within inside ring $P^-$. This error term is small only if most pixels within inside ring $P^-$ are of uniform intensity and close to maximum brightness $I_{max}$.

The second error term corresponds to the expectations for outside ring $P^+$. In this region, the brightness should also be relatively constant, since the antibiotic should be affecting the culture uniformly. However, the average value within this region is uncertain and depends on the interaction between the organism and the antibiotic. Thus the mean value of brightness within ring $P^+$, $I_{ave}(P^+)$ is calculated and the average squared difference from this value is calculated in step 142.

$$E^+ = \frac{\sum_{(x,y) \in P^+} (I(x,y) - I_{ave}(P^+))^2}{N(P^+)} \quad (4)$$

where $N(P^+)$ is the number of pixels within outside ring $P^+$, and $I_{ave}(P^+)$ is the average brightness intensity within outside ring $P^+$. Since at the transition, both $E^-$ and $E^+$ should be satisfied, the sum $E = E^- + E^+$ is used as the total error metric. The transition radius between B and C, $r_{BC}$, is selected in step 144 as that radius value for which error metric E is minimized.

The results of the automated inhibition zone estimation procedure are presented to the operator in a window on the monitor of the video display station 56 (FIG. 2). The results are represented as graphic overlays on the electronic image. For each antibiotic disk, a circle of a distinctive color is drawn centered on the disk and of radius equal to the estimated inhibition zone radius.

By controlling a computer mouse or other pointing device, the user can modify the results of the estimation procedure by a single mouse click as follows. The operator points to a location on the boundary of the inhibition zone of a selected antibiotic disk. The system then calculates the distance between the mouse click location and the center of each disk. The disk which is closest is presumed to be the disk to be modified. The distance between the mouse click location and this disk center is used as the new estimate of the inhibition zone radius. In addition to the graphical representation, the operator is presented with a text field which indicates the estimated inhibition zone radius in millimeters for each antibiotic. If the radius values are modified by the operator as described above, the text field is updated accordingly.

The system can store and retrieve previously acquired electronic images and the results of the image processing function in storage unit 58. This archival storage can be organized by date, patient, or assay type.

While there have been shown and described what are at present considered the preferred embodiments of the present invention, it will be obvious to those skilled in the art that various changes and modifications may be made therein without departing from the scope of the invention as defined by the appended claims.

What is claimed is:

1. Apparatus for estimating antibiotic effectiveness from an antibiotic diffusion sample comprising a plate having a medium containing a population of a test organism and a plurality of antibiotic disks positioned on said plate in said medium, each of said antibiotic disks being impregnated with an antibiotic whose effectiveness is to be estimated, an inhibition zone surrounding each of said antibiotic disks after a predescribed incubation period, said apparatus comprising;

a light source for illuminating said antibiotic diffusion sample;

a video camera for acquiring an image of said illuminated antibiotic diffusion sample; and an image processor for analyzing said image, said image processor including an electronic digital computer comprising:

means for determining locations of said antibiotic disks in said image;

means for determining an average brightness and a brightness variance of said image in a region surrounding each of said antibiotic disks; and means for estimating a radius of an inhibition zone surrounding each of said antibiotic disks from said average brightness and said brightness variance, thereby providing an estimated radius of said inhibition zone which is indicative of antibiotic effectiveness.

2. Apparatus for estimating antibiotic effectiveness from an antibiotic diffusion sample comprising a plate having a medium containing a population of a test organism and a plurality of antibiotic disks positioned on said plate in said medium, each of said antibiotic disks being impregnated with an antibiotic whose effectiveness is to be estimated, an inhibition zone surrounding each of said antibiotic disks after a prescribed incubation period, said apparatus comprising:

a light source for illuminating said antibiotic diffusion sample;

a video camera for acquiring an image of said illuminated antibiotic diffusion sample; and an image processor for analyzing said image, said image processor including an electronic digital computer comprising:

means for determining locations of said antibiotic disks in said image;

means for determining an average brightness and a brightness variance of said image in a region surrounding each of said antibiotic disks; and means for estimating a radius of an inhibition zone surrounding each of said antibiotic disks from said average brightness and said brightness variance, thereby providing an estimated radius of said inhibition zone which is indicative of antibiotic effectiveness, said means for estimating the radius of the inhibition zone comprising:

means for defining a inside ring between r–d and r, and an outside ring between r and r+d, where d is less than r, for first radius values r between the radius of the antibiotic disks and a maximum radius;

means for determining, for said first radius values, a first ratio of brightness variance to a minimum brightness variance between the radius of the antibiotic disk and the maximum radius, and for retaining second radius values of said first radius values for which the first ratio is greater than a first threshold value;

means for determining, for said second radius values, a second ratio of average brightness in the outside ring to average brightness in the inside ring, and for retaining third radius values of said second radius values for which the second ratio is greater than a second threshold value;

means for determining, for said third radius values, a first error value representative of an average squared difference between a brightness at each pixel and the inside and the maximum brightness;

means for determining, for said third radius values, a second error value representative of the average squared difference between a brightness at each pixel in the outside ring and the average brightness in the outside ring; and means for selecting as the radius of said inhibition zone one of said third radius values for which a sum of said first error value and said second error value is minimized.

3. Apparatus as defined in claim 2 further including an optical filter positioned between said light source and said antibiotic diffusion sample for illuminating said antibiotic diffusion sample with radiation in a selected wavelength range.

4. Apparatus as defined in claim 2 further including an optical filter positioned between said antibiotic diffusion sample and said video camera, said optical filter having a passband in a selected wavelength range.

5. Apparatus as defined in claim 2 wherein said means for determining locations of said antibiotic disks comprises:

means for determining a number of pixels in said image covered by said antibiotic disks from knowledge of a number of antibiotic disks, their diameters and an approximate spatial resolution of said image;

means for ordering the pixels in said image from said lowest brightness to highest brightness;

means for determining a threshold value such that all the pixels in said image covered by said antibiotic disks have brightness values less than said threshold value;

means for defining a binary image $C(x,y)=1$ if the brightness of the pixel is less than the threshold value, else $C(x,y)=0$, where C represents values of the binary image, and x and y represent horizontal and vertical coordinates, respectively, of a pixel in said image;

means for determining areas and coordinates of centroids of connected regions having a value of one in said binary image; and means for identifying a number $N_d$ of largest connected regions having a value of one in said binary image as said antibiotic disks, where $N_d$ is the number of antibiotic disks on the plate.

6. Apparatus as defined in claim 5 wherein said image processor further includes means for determining the radius of each of said antibiotic disks in said image.

7. Apparatus as defined in claim 2 wherein said image processor further includes means for associating each of said antibiotic disks in said image with an antibiotic by comparison of said image with a predefined template including information as to antibiotic disks locations and corresponding antibiotics.

8. Apparatus as defined in claim 2 wherein said image processor further includes:

means for defining a template which contains a nominal disk center location of each of said antibiotic disks at an arbitrary rotational orientation and an antibiotic descriptor associated with each of said antibiotic disks;

means for determining a rotation angle, to be applied to nominal disk center locations in the template, that minimizes a difference between locations of said antibiotic disks in said image and the nominal disk center locations in the template rotated by said rotation angle; and means for labeling each of the antibiotic disks in said image with an antibiotic descriptor from said template by associating each of said antibiotic disks in said image with a closest disk from the rotated template.

9. Apparatus as defined in claim 2 further including:

a video display system including a display screen and a pointing device;

means for displaying the image of said antibiotic diffusion sample on said display screen;

means for displaying the estimated radius of the inhibition zone surrounding said antibiotic disks on said display screen; and means for overriding the estimated radius of the inhibition zone of one or more of said antibiotic disks in response to a user positioning a cursor at a desired location on said display screen and operating the pointing device, thus permitting the user to manually specify an inhibition zone based on direct inspection of the image of said antibiotic diffusion sample.

* * * * *